US009162076B2

(12) United States Patent
Kumar

(10) Patent No.: US 9,162,076 B2
(45) Date of Patent: Oct. 20, 2015

(54) METHOD FOR TISSUE REGENERATION OR DEGENERATION IN HUMAN AND AN APPARATUS THEREFORE

(76) Inventor: Rajah Vijay Kumar, Bangalore (IN)

( * ) Notice: Subject to any disclaimer, the term of this patent is extended or adjusted under 35 U.S.C. 154(b) by 1877 days.

(21) Appl. No.: 11/569,917

(22) PCT Filed: Jun. 7, 2004

(86) PCT No.: PCT/IN2004/000157
§ 371 (c)(1),
(2), (4) Date: Dec. 1, 2006

(87) PCT Pub. No.: WO2005/120171
PCT Pub. Date: Dec. 22, 2005

(65) Prior Publication Data
US 2007/0208249 A1   Sep. 6, 2007

(51) Int. Cl.
  *A61N 2/02* (2006.01)
  *A61N 2/00* (2006.01)
  *A61N 1/04* (2006.01)
  *A61N 1/32* (2006.01)

(52) U.S. Cl.
  CPC .............. *A61N 2/004* (2013.01); *A61N 1/0412* (2013.01); *A61N 2/02* (2013.01); *A61N 1/327* (2013.01)

(58) Field of Classification Search
  CPC ........... A61N 2/00; A61N 2/02; A61N 2/002; A61N 2/004
  USPC .......... 600/9–15, 410–423; 250/492.1–492.3; 378/146–161; 607/100–102, 154–156
  See application file for complete search history.

(56) References Cited

U.S. PATENT DOCUMENTS

| 4,672,951 | A | | 6/1987 | Welch |
| 5,099,756 | A | * | 3/1992 | Franconi et al. ................. 600/10 |
| 5,247,936 | A | | 9/1993 | Hagiwara |
| 5,453,074 | A | * | 9/1995 | Imoto .............................. 600/15 |
| 6,048,302 | A | * | 4/2000 | Markoll ........................... 600/13 |
| 6,461,289 | B1 | * | 10/2002 | Muntermann .................... 600/9 |
| 6,470,220 | B1 | * | 10/2002 | Kraus et al. .................... 607/103 |
| 2003/0088189 | A1 | * | 5/2003 | Tu et al. ......................... 600/549 |
| 2003/0195410 | A1 | * | 10/2003 | Winter ........................... 600/410 |
| 2004/0022732 | A1 | * | 2/2004 | Zotz et al. ..................... 424/9.34 |

FOREIGN PATENT DOCUMENTS

CN    1077655 A    10/1993

OTHER PUBLICATIONS

Hornak, JP. The Basics of NMR. Jan. 1, 1998, 3 pages.*

* cited by examiner

*Primary Examiner* — Catherine B Kuhlman
(74) *Attorney, Agent, or Firm* — Laurence P. Colton; Smith Risley Tempel Santos LLC

(57) ABSTRACT

Disclosed herein is an apparatus for tissue regeneration or degeneration in human by applying rotational field narrow focused quantum magnetic resonance on the required area. The apparatus consists of a plurality of guns for delivery the quantum magnetic resonance, a traveling platform for carrying the person under treatment, an electronic switching system for controlling the guns, said electronic switching system being controlled by a main computer through an on board microprocessor and means for cooling and dispersing the heat generated during the operation.

7 Claims, 4 Drawing Sheets

CARTILAGE THICKNESS
BEFORE EXPOSURE WAS
EQUAL TO 7 PIXELS

CARTILAGE THICKNESS
AFTER EXPOSURE WAS
EQUAL TO 19 PIXELS

A TUMOR MEASURING 74mm x 73mm
BEFORE RFQMR EXPOSURE

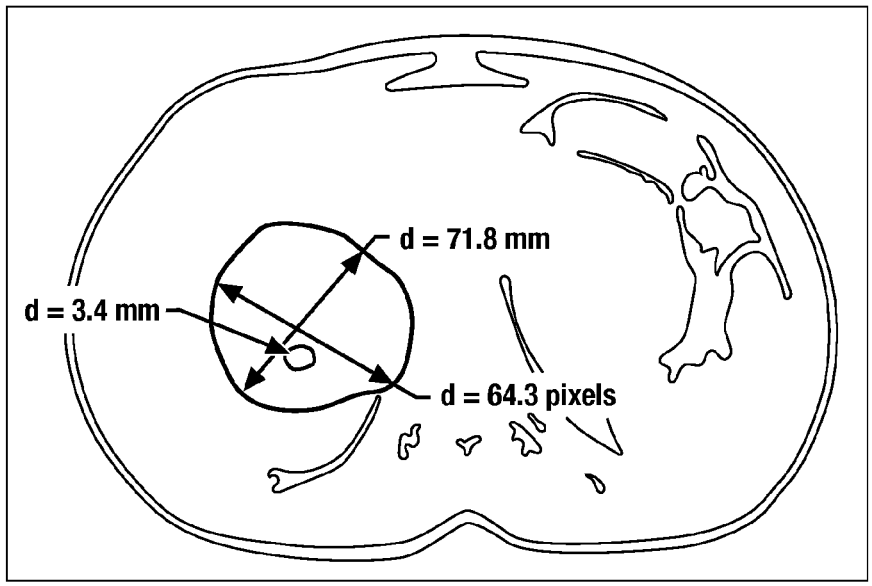

THERE IS NO SIGNIFICANT CHANGE IN TUMOR SIZE AFTER 15 DAYS OF EXPOSURE, BUT THERE IS AN OVERALL CHANGE IN THE TEXTURE AND A SMALL NON-SPECIFIC CONTRAST CHANGE OF ABOUT 3.4mm SEEN AFTER 15 DAYS OF RFQMR EXPOSURE

*FIG. 7*

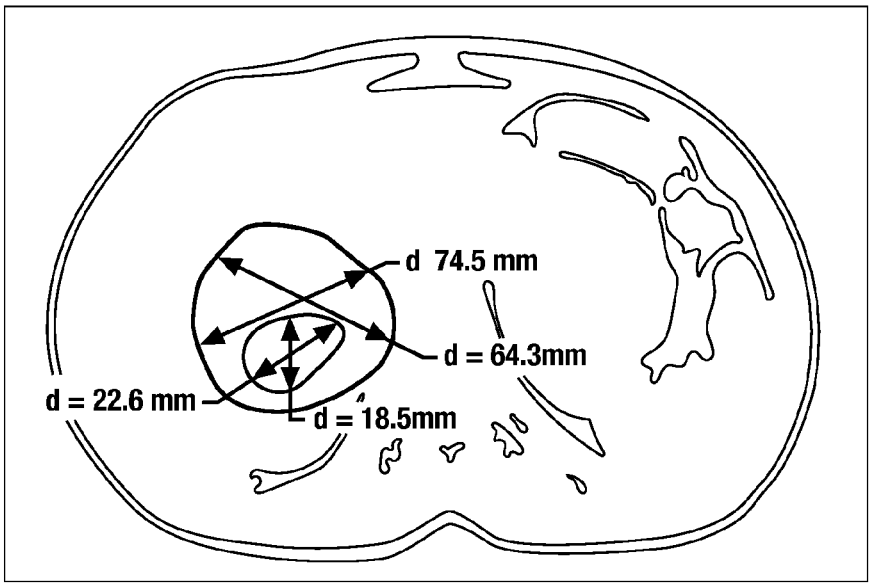

THOUGH THERE IS AGAIN NO SIGNIFICANT CHANGE IN THE TUMOR SIZE, THERE IS A SIGNIFICANT PRESENCE OF TISSUE NECROSIS, MEASURING 18.5mm x 22.6mm. THIS CONFIRMS THAT RFQMR DEGENERATION KIND OF IMPLODES THE TUMOR FROM THE CORE.

*FIG. 8*

METHOD FOR TISSUE REGENERATION OR DEGENERATION IN HUMAN AND AN APPARATUS THEREFORE

CROSS-REFERENCE TO RELATED APPLICATIONS

Priority is hereby claimed to co-pending PCT application Serial No. PCT/IN2004/000157, filed 7 Jun. 2004.

TECHNICAL FIELD

This invention relates to a method for tissue regeneration or degeneration using rotational field narrow focused quantum magnetic resonance in human as well as a machine for carrying out the said method. The said machine produces high power multi frequency rotating electromagnetic beams, modulated with finely derived frequency amplitude and field strength based on the specific cell types and application that are precisely focused to the target area of repair. Throughout the specification, the term "Rotational Field Narrow Focused Quantum Magnetic Resonance" is referred to as "RFQMR".

Regeneration refers to the ability of the body to renew or reproduce cells and tissue with renewed life and vigor and degeneration refers to slowing down of cell growth in pathologically hyper reproductive tissues. While tissue regeneration helps in treating affected areas such as cartilages, bones etc., tissue degeneration helps in retarding the growth of the living cell and stop the growth of unwanted blood vessels etc. Tissue regeneration helps in treating problems associated with old age or accidental injuries whereas tissue degeneration helps in treating cancer, obesity, tumor etc.

BACKGROUND OF INVENTION

A lot of research is being done on tissue/cell degeneration and regeneration. Bone tissue regeneration to repair bone defects, whether they are the result of injury, surgery, disease or old-age, has been a common goal of medicine and dentistry. In dental field, the grafting has been more popular. Conventionally, filling the affected bone with graft material and covering the graft material with a barrier material to exclude competitive cells can achieve bone tissue regeneration.

Three different graft materials are used in bone tissue regeneration, i.e. (i) A live active bone tissue, (ii) demineralized, freeze-dried, allogenic bone and (iii) autogenous cortical bone chips. However, there exists a need to regenerate bone tissue in a reliable manner without undue risk of infection and without the need for prolonged and multiple operative procedures.

Degeneration can also be done in a number of ways. For example, for treatment of cancer cells or tumor, chemotherapy or radiation etc are used. However, some of these therapies have serious side effects and the same is not recommended to many persons suffering with cancer or tumor, and the like.

It has been known to use magnetic therapy in both cell regeneration and/or degeneration. Magnetic fields are nothing new and they are a part of all basic life processes. Scientists have discovered as to how to focus and shape magnetic fields that occur in nature in order to stimulate cell metabolism and bring about healing and recovery. Magnetic fields affect symptoms by going straight to the source-body cells. Magnetic resonance treatment is a scientific refinement available for the present generation.

A system has been known for the last few years which allows the body to be exposed to pulsating low frequency magnetic fields that stimulates cell metabolism, increases the oxygen assimilation and accelerates the removal of toxic chemicals and waste. Depending the condition and sensitivity of the person, improvement could be noticed between 2 to 8 weeks.

Electromagnetic stimulation of sensory nerves or acupuncture points has focused mainly on stimulation of nerve tracts for the purpose of promoting release of natural opiates or pain pathway blocks through gating mechanisms. Various forms of such stimulation have been tried such as application of voltages or currents to acupuncture needles, transcutaneous electrical nerve stimulation (TENS), pulsed magnetic field stimulation, local application of heat or cold, use of light radiation, and magnetic therapy. Prior art devices of this type include the use of low frequency magnetic pulses as described in U.S. Pat. No. 6,234,953 B1, issued May 22, 2001.

None of the above described adopt the principle of rotational field quantum magnetic resonance. Application of magnetic resonance to the affected area either to regenerate or degenerate the cells as the case may be, is the field of study of the present invention. In the present system, the quantum magnetic resonance applied is tissue specific and further it has no side effects.

Accordingly, the primary object of the present invention is to develop a method for tissue regeneration or degeneration using rotational field narrow focused quantum magnetic resonance. A further object of the present invention is to provide an apparatus for treatment using the said method.

SUMMARY OF THE INVENTION

This invention thus provides a method for tissue regeneration or degeneration in human using rotational field narrow focused quantum magnetic resonance depending on the cell type and their permittivity.

This invention further provides an apparatus for applying rotational field narrow focused quantum magnetic resonance on the required area of treatment comprising means of generating the quantum magnetic resonance, means for delivering the magnetic resonance which comprises of a plurality of guns, an electronic switching system for controlling the guns, said electronic switching system being controlled by a main computer through an on board microprocessor and means for cooling and dispersing the heat generated during the operation.

Rotational field narrow focused quantum magnetic resonance is an effective, non-invasive solution in the treatment of Osteoarthritis, relieving pain and disability due to trauma, temporo-mandibular joint disease, tinnitus, peridontal disease, carpal tunnel syndrome, osteoporosis, tendonitis and convalescence following surgical repair of ligaments, fresh bone fractures in elderly, aseptic necrosis, fibromyalgia, sciatica, post-polio syndrome, migraine, metatarsalgia, acute burns, immune deficiency disorders, drug resistant epilepsy, diabetic neuropathy, herniated disk, problem wound healing, Stimulation of Angiogenic Growth Factor and promoting Coronary and peripheral pro-angiogenesis and retarding the Angiogenic Growth Factor to promote Anti-Angiogenesis in Cancer.

Another possible application of RFQMR is Electroporation. Electroporation involves directly applying RFQMR pulses of millionths of a second duration and field strength of 100-1500 volts per centimeter to living cells. These pulses cause nanoscopic pores to open up through the cell's membrane. When the pulse stops, the pores close again, trapping the drug or DNA inside the cell. Applying the RFQMR pulses either directly to the target tissue to be treated in a living organism, or to cell suspensions and isolated organs can carry out Electroporation. This application of RFQMR may go a long way, as it will open up the potential for new approaches to medical problems where successful treatment depends on finding ways for the therapeutic molecules to reach the cell interior. This includes—among others—treatments such as cancer chemotherapy, the delivery of DNA for gene therapy and DNA vaccines, the delivery of drugs for treating cardiac and vascular problems as well as the treatment of the eye disease. Further research can bring about many other potential applications such as the treatment of haemophilia and other genetic defects or the treatment of cardiovascular diseases and the prevention of atherosclerosis can be explored.

RFQMR in Tissue Degeneration:

The higher end of Electromagnetic Radiation has long been used in the treatment of cancer, but there is an interesting spectrum of Electromagnetic field, at the lower end of the spectrum, when delivered in the appropriate manner, can regenerate living cells, grow new blood vessels, regenerate tissues and at the same time, when the spectral characteristics and delivery system is altered, do the reverse of all the above, degenerate the living cell, stop the growth of new blood vessels etc.

Rotational Field Narrow Focused Quantum Magnetic Resonance is a new machine, that produce high power multi frequency rotating electromagnetic beams that are precisely focused to the target area of repair. There are totally 96 beams delivering the correct dosage.

There is a wide agreement in the scientific community on the damage and cancer causing effect of radiation in the ionising region of the Electromagnetic spectrum ($>10^{15}$ Hz or above) in the Ultraviolet region. The Heating effect of microwaves on tissue is known. It is now understood that Controlled Quantum Magnetic Resonance can Accelerate or Decelerate growth.

The Hypothesis is one of biosynthesis involving the formation of new chemicals affected by RFQMR signals altering the atomic properties with in the living cells.

If one considers a living cell as having a diameter of about 10 micrometers and subjected to a RFQMR field, the effect is one of an increase in the rate of protein production, including enzymes. One way this appears to happen involves a two-stage process involving transcription and translation.

In the transcription stage the DNA unravels partially forming messenger RNA, (mRNA) that goes out of the DNA nucleus and latches into the ribosome in the cell fluid surrounding the DNA nucleus. In the second stage the protein is produced. There is also a feedback mechanism that control how much of protein enzymes are produced, depending on the body's needs. Protein production or enzyme activity seems to increase in the presence of a RFQMR field.

There is a known mechanism, formerly known as heat shock, whereby a cell produces extra protein/enzymes in response to shock such as thermal shock. These proteins are called heat shock proteins (HSPs). This is now referred to as a stress response rather than heat shock because the process apparently applies to any stress, not only thermal. RFQMR radiation appears to be merely another form of stress on the cell.

One interesting result is that the response from increasing the RFQMR field in a cell from 8 milligauss to 80 milligauss is similar to the effect of increasing the temperature from 37 deg C. to 42 deg C.

Another interesting effect is the stress tolerance. When a cell has its temperature raised from 37 deg C. to 45 deg C. the cell will die within a few minutes. But if the cell's temperature is raised first to about 42 deg C., allowed to fall back to 37 deg C. then raised to 45 deg C. the cell doesn't die, as if, the memory of the previous stress has conditioned the cell to cope with more stress than before.

There also appears to be a negative feedback mechanism operating whereby the HSPs reduce the rate of production of further HSPs. What are the implications for these effects with RFQMR radiation? Does this mean that people subjected to continuous or occasional RFQMR radiation are more able to tolerate further Electromagnetic radiation?.

What is happening at the molecular level? It appears that the process is one affecting the Sodium Potassium Adenosine Triphosphatase (Na—K-ATP-ase) pump that drives the cell.

Consider a continuous cell membrane (phospho-lipase). There are molecules that cross the membrane with one particular pear-shaped one having its narrow end extending beyond the outer edge of the membrane and its broader end extending beyond the inner edge. This is the larger of a two-part molecule; the pear-shaped one is accompanied by a smaller elliptical part. Most of the interesting characteristics of the molecule occur in the part.

For this 100,000 molecular weight cell the ATP converts to ADP with the production of 3 Na+ ions and 2 K+ ions.

It is the business of these enzymes to use the energy from the ATP to get the Na to move out of the cell and the K to move inside. It appears to do this by modifying the permeability of the cell walls to allow these interchanges.

This enzyme activity appears to be related to the movement of electric charge e–. Thus the movement of these negative charges probably mediates the movement of these positive ions through the cell membrane and the amount of activity enhancement depends on the availability of these charges.

The enzyme activity is enhanced for magnetic fields at all enzyme activities but for electric fields is limited to low enzyme activity. Any electric field present does not permeate the membrane. Instead it builds up a +ve charge on the outer layer of the membrane. Its ability to produce a corresponding –ve charge on the inner surface of the membrane relies on the scavenging of free charges within the membrane. So this enhancing effect is limited to low enzyme activities presumably because of the limitation of the availability of sufficient free charges within the membrane.

Hypothesised Mechanism:

It is thought that the chromosomes, following the messages received as a result of the variations of potential (–70 to –90 mV normal, –40 to –60 when infected, –20 to –30 in cancer and 0 when dead) in the cytoplasmic membrane, activate through electromechanical effects (stress responsive), the emission of messages by the genes that regulate cell dynamics for normal cell functions or for the mitochondrial activities for ATP production. An electrical equivalent circuit composed of a zener diode attached to the base of a bipolar transistor is offered as a model for the operation of the mitochondrion. The zener diode represents the on/off pulse operation of some cell functions, the combined circuit impedance represents the impedance of the glycoproteinic sensors present on the mitochondrial membrane, and the transistor represents the ATP activation process.

It is supposed that the excessive production of ATP is related to an alteration of the glycoproteinic sensors present on the mitochondrion membrane with consequent lowering of the impedance that in turn does not discriminate between the signals in frequency and activates the production of ATP in an almost continual way. The cancer cell would therefore go into mitosis due to the excess of ATP.

RFQMR fields are used to act on the mitochondrial membrane, increasing the impedance of the glycoproteinic sensors through the lengthening of the polyglycidic chain. The spin of the RFQMR field is used to interfere with the communications between the genes and the protoplasmic glycoproteinic complexes involved in the promotion of cell mitosis.

It is thought that the impedance of the mitochondrial membrane to the messages coming from the genes increase with the RFQMR treatment and with increase in the malignancy (the highest impedance for undifferentiated tumours). This is related to a greater alteration of the sensors of the undifferentiated tumours and therefore to their greater predisposition to the bond with polyglycidic chains. The undifferentiated cancer cells, because of the high impedance induced on the mitochondrial membrane by the RFQMR exposure, it stops producing ATP and therefore 'possibly' enter into necrosis. Following the treatment the differentiated cancer cells have an impedance which is still sensitive to some messages coming from the chromosomes promoting the normal production of ATP, so these cells change their state of mitosis; however, they continue to live in a quiescent state (vegetative form of life). The normal cells are not influenced by the RFQMR radiation treatment as the impedance of their mitochondrial sensors is not modified and remain sensitive to messages that arrive from the chromosomes for the activation of the ATP synthesis.

Influence of RFQMR Radiation on Cell Functions in Degeneration:

Tissue Degeneration is mainly useful in the treatment of Pathologically Hyper Reproducing Tissues, like a tumor in a cancer patient. RFQMR basically alters the Membrane potential of the tumor cells thus halting Mitosis (cell division).

The preliminary observations conducted in vitro show an alteration of cell morphology, a halt to proliferation, fusion, and necrosis in lymphoblastoid cell lines, and in some neoplastic lines, after treatment with specifically modulated QMR radiation (HeLa, mammary carcinoma, CCL-178, colon adenocarcinoma, H 23, H 32, h 12.1, 1411 H, testicle carcinoma, M 5, M51, stomach carcinoma, MCF-7 human Caucasian breast adenocarcinoma ECACC 86012803, normal cell line, and MDBK bovine kidney cells).

It is known that cells communicate with each other by means of direct metabolic exchanges or through the transfer of ions or molecules that act as messengers. Multi-cell signals, which originate in the interaction of ligands with membrane receptors, can activate a closely connected series of biochemical reactions. The biological membranes represent multi-molecular operative structures, and even a slight alteration in the composition of the membrane can lead to significant changes in its functions. RFQMR radiations can influence this communication between cells and within the cells themselves due to their ability to activate or change the motion of the electrical charges. In fact, an increasing amount of literature illustrates the possibility of inducing biological effects in cells when appropriate electrical and electromagnetic fields are applied to have a direct effect on the membranes.

Among the various effects obtained are those on Na+ and K+ dynamics and their role in ATPasi, as well as the effects on the intermembrane exchanges of the Ca++ ion, which, because of its presence in most biomolecular processes, has earned the name of second messenger. Moreover, exposure conditions that have led to effects on the membrane permeability of the Ca++ ion have shown a negative influence on the mitotic fuso, and this influence is selectively tied to the characteristic of the quantum electromagnetic field used. Up to now, the results obtained imply that the membrane receptors (e.g., the gluco-protein complexes), are able to decipher quantum signals at a well defined frequency and amplitude by reacting in a specific way. The energy transformed form the fields are absorbed and directly coupled to guide biochemical reactions. These results have served as the bases for some applications in the therapeutic field, particularly in the reproduction of cartilage tissue. This is due to the fact that the activation of some cell functions is bound to quantum signals of the on/off type, that is, not with linear but with modulated non-sinusoidal wave shapes. The quantity of charge/current density involved is quite large being equivalent to currents in a conductor of about 10,000 amperes; perhaps approaching superconductivity.

The Following are the Typical Steps Involved in the Treatment of a Cancer Patient Using RFQMR:

The patient is first diagnosed for cancer using the conventional methods. A biopsy is done to establish the type of cancer cells and their morphology. A MRI of the affected region or a whole body MRI is done depending on the type of cancer (some cancer cells spread faster than the other or like some tumor cells spread through the circulatory system and some will spread through the lymphatic system).

The radiologist and the oncologist will decide on the primary site of the cancer, and decide on the "Tumor of first Attack". The radiologist will then prepare the "Target Planning Films", this is derived from the MRI slices, that shows the core of the tumor and then he will position all the 96 QMR guns in firing position. These films are given to the Engineers who apply RFQMR.

The Engineers then plan the RFQMR Dose Parameters from the TPF. The patient is then sent for physical marking to the radiologist, who will physically mark the exact location of the tumor under the control of a computerised tomography.

The patient is then put on the RFQMR machine and a template is made out of a special transparent plastic sheet. The first exposure starts on the same day or on the next day.

On the day of the exposure, the patient is made to lie down on the RFQMR machine and is rolled in, the guns are now focused at the target using a laser guided system.

The exposure is for 1 hour each day for 28 days. Every 7 days the echogenicity of the tumor is assessed using an ultra sound and the blood tests are repeated. MRI is done on the 15th and 30th day to assess the Tumor Necrosis. The tumor is expected to get necrosed from the core of the tumor, a kind of implosion. After the 28 days treatment, the patients gets back to his or her normal life, the patient is further assessed after 6 weeks after the last exposure.

RFQMR in Tissue Regeneration:

Tissue Regeneration is more or less the opposite of the tissue degeneration. This has a wider application then Degeneration, application can be in Osteoarthrites, Grow new blood vessels where required, wound healing, treating non healing fractures etc., In Tissue Regeneration, RFQMR is simply used in the somewhat reverse gear. Depending on the type of the cell type, and their permittivity, RFQMR exposure is planned. Most of the expected reactions are reverse of what is mentioned above. Though the hypothesis of regeneration may be different for different tissue types, we can comment on the tissue regeneration in human cartilage cells.

Hypotheses of RFQMR Theory in Cartilage Regeneration:

Like other tissues, bone and cartilage are constantly being built up and broken down by a variety of metabolic and physical influences. The major stimulus for bone and cartilage formation is a piezoelectric signal generated when these structures are subjected to tension or compression. This explains why bone atrophies in the absence of any significant pressure, such as weightlessness during space travel or immobilization in a cast. The transmission of this signal is also impaired following joint injury due to, trauma or diseases such as osteoarthritis. RFQMR is designed to characterize and reproduce the piezoelectric signal that initiates these regenerative activities by the induction of a spin in the hydrogen atoms thus creating a streaming potential in the extracellular matrix (ECM) when bone or cartilage are placed under a load. In other words, when you take a step, putting weight on the joint, the cartilage is compressed, the fluid gets displaced, and it carries with it mobile ions, the sodium ions, leaving behind the negatively charged proteoglycan carboxyl and sulfate ions. That generates a electric potential because you have unneutralised negative charges. This is called a streaming potential. RFQMR can recreate this streaming potential and its restorative rewards in joints impaired due to disease or trauma even though they are at rest. Preliminary clinical trials have shown that, patients with severe Osteoarthritis have achieved cartilage regeneration ranging from one to three millimeters in 21 days of exposure to RFQMR.

The exact expected mechanism in tissue regeneration in cartilage cells i.e. the Method of RFQMR exposure is shown in FIGS. 2a to 2c.

Figure 1A:
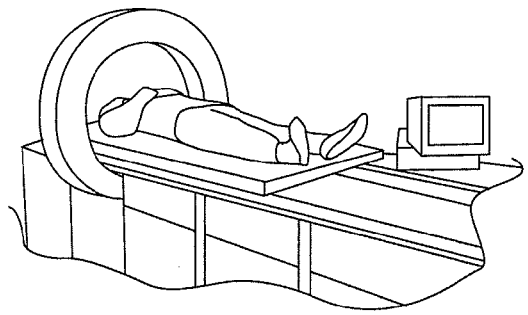

Rotational Field Narrow Focused Quantum Magnetic Resonance is administered using the RFQMR machine illustrated in the drawings.

Figure 1B:
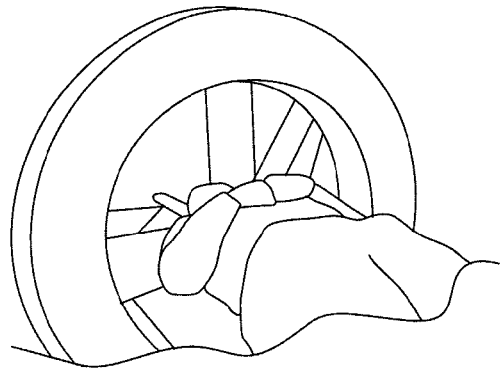
Figure 2A:
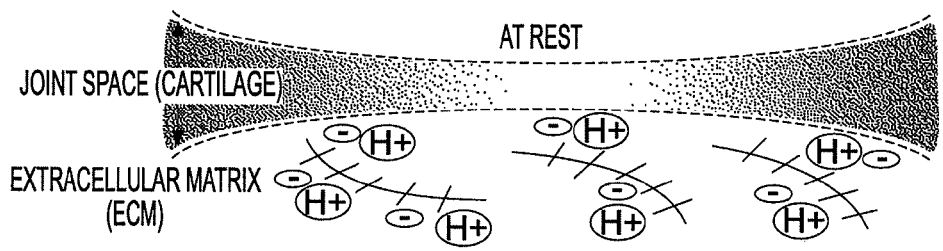
FIG. 2a shows the change in equilibrium between hydrogen protons and negative charge carriers in the extracellular cartilage matrix—NO Streaming Potential—at rest.
Figure 2B:
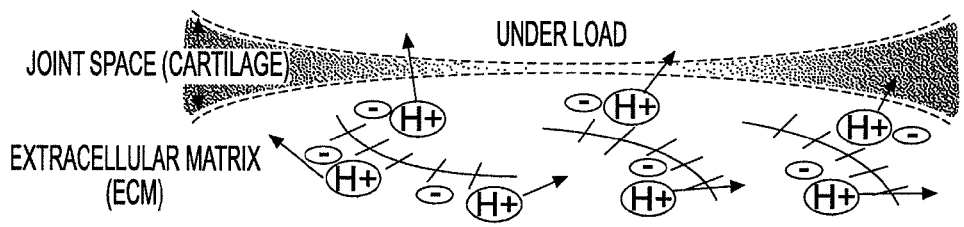
FIG. 2b shows the creation of a streaming Potential in the ECM during loading caused by the compression of fixed negative charged fluid forced out of cartilage tissue with forced influx of Hydrogen Protons under load.
Figure 2C:
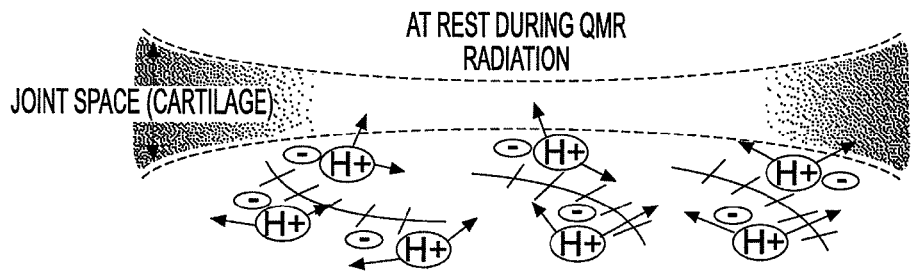
FIG. 2c shows the generation of streaming voltage potentials flow in the joint caused by forced movement of hydrogen Protons in the ECM caused by the alteration in RFQMR spin in the Hydrogen Atoms, as a stimulation of Chondrocytes in the ECM at rest during quantum magnetic resonance radiation.
Figure 3:
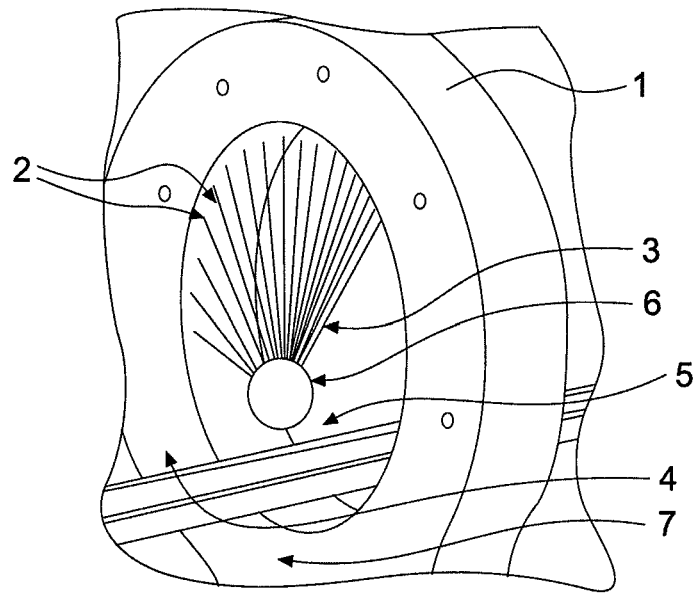
Figure 4:
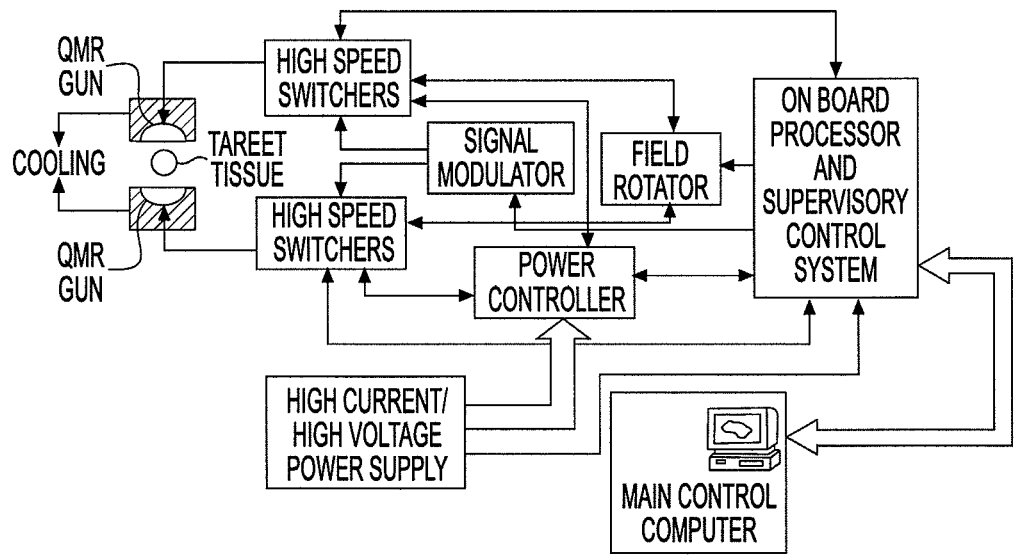
Figure 5A:
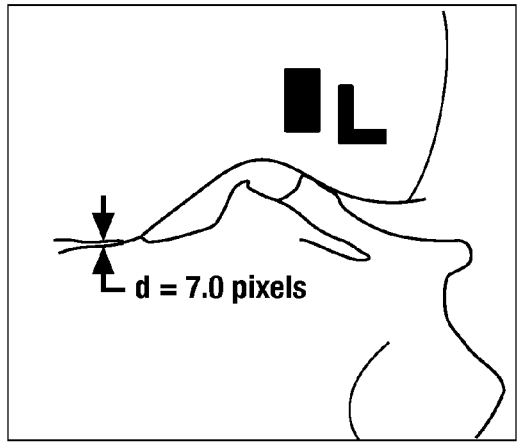
Figure 5B:
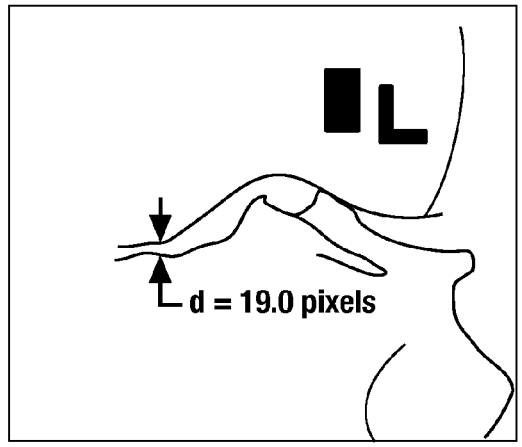
Figure 6:
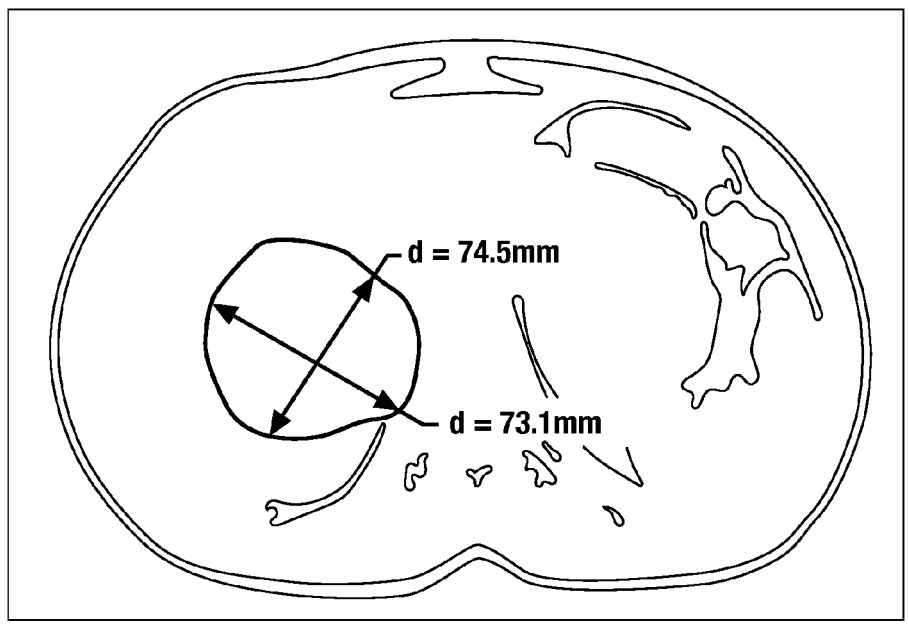

In the drawings:

FIG. 1 illustrates the general layout of the RFQMR machine of the present invention;

FIG. 2a to 2c illustrate the Mechanism of the effect of RFQMR spin on the chondrocytes;

FIG. 3 illustrates the RFQMR head along with other controls used in the machine;

FIG. 4 illustrates the block diagram of the RFQMR machine of the present invention;

FIG. 5 illustrates the visible changes in the patient's knee before and after the RFQMR treatment for tissue regeneration; and FIGS. 6 to 8 illustrate the various changes in the patient's tumor before, during and after the RFQMR treatment for tissue degeneration.

One can observe that the RFQMR machine of the present invention looks like a MRI or CT machine (see FIG. 1). The affected joint (knee) is placed inside RFQMR machine and the desired exposure characteristics (like the cartilage to bone gap, skin to cartilage distance, Name, age, gender, height and weight etc., in regenerative RFQMR or the distance to the tumor core, and details of other cell type around the tumor etc., is obtained using a Magnetic Resonance Imaging (MRI) in case of a Degenerative RFQMR) are fed into the computer, the computer then computes various wave front and spin frequencies, pulse amplitudes, field strength etc., there after the operator will precisely focus the beams, with the aid of the subject's x-rays in case of a regenerative RFQMR or the patient is precisely marked using a CT-scan in case of a degenerative RFQMR. The treatment is for 60 minutes daily for a period of 21 days in case of regenerative RFQMR or 28 days in case of degenerative RFQMR, depending on the RFQMR purpose, outcomes are evaluated by x-ray and other methods, at the end of the treatment. The treatment is to be uninterrupted.

The Subjects do not feel any pain or discomfort during the treatment, the field strength on the body surface is periodically measured by the computer, and if there is any deviation, it will alarm, change in field strength may be because of absence of a beam, In all 96 QMR-beams are used at an angle of 11.25 degrees.

FIG. 1 shows the details of the RFQMR machine, the circular part of the machine is called the QMR head 1, which consists of 96 QMR generators 2 i.e. guns made of a special metal alloy. These QMR guns produces the QMR beams 3 and are mounted on a Heat sinking material to disperse the heat generated as fast as possible. The heat sink is further cooled using an appropriate cooling system 4, such as air circulators. The patient bed 5 is a traveling platform surfaced with sponge and leather to provide comfort to the patient. The target area is marked by reference numeral 6.

The 96 guns are controlled by appropriate electronic control system and switching system, generally marked by reference numeral 7, which is capable of handling high voltage and currents. The switching system is controlled by an on board microprocessor, which receives instruction from the main control computer.

The Main Control Computer has software designed for the purpose of planning the RFQMR exposure dose and precise focusing and targeting. The RFQMR can be applied in almost all degenerative disease.

Explanation of the Block Diagram of the Rotational Field Quantum Magnetic Resonance Tissue Engineering System Shown in FIG. 4:

The RFQMR system consists of the following sub-systems:

1. On Board Microcontroller based Supervisory Control System (SCS)
2. High Current/High Voltage Power supply sub-assembly
3. Power Controller sub-assembly
4. High speed switching sub-assembly
5. Signal Modulator
6. Field Rotator
7. QMR guns with cooling sub-assembly
8. Main Control Computer On Board Microcontroller based supervisory control system is the main processing part of the RFQMR system. This sub-assembly receives the commands pertaining to the dose such as wave front frequency, spin frequency applied field strength etc. from the main control computer. This information is computed and made suitable to be transmitted to the Signal Modulation, field rotator and High speed switching sub-assemblies.

High Current/High Voltage Power supply is a sub-assembly that takes in the AC 230 volts power from the mains and converts into various high voltage low current as well as high current low voltage power sources for the operation of various sub-assemblies as well as the RFQMR guns. This sub-assembly is the energy source for the entire system.

Power Controller sub-assembly receives the power from the HCHV power supply and controls the distribution of the same to the various other sub-assembly under the command and control of the SCS. It also takes care of the safety aspects, like over loads, temperature or thermal shutdown etc. for the safe running of the system.

High Speed Switching Sub-Assembly receives multiple inputs from signal modulators and field rotators and operates under the command and control of the SCS. The HSS sub-assembly is capable of handling high voltages and currents and switch them on and off at very high frequencies, thus is capable of producing fine modulated pulses of millionth of a second. This sub-assembly directly fires the QMR guns, under the instruction and regulation of the SCS.

Signal Modulator Sub-Assembly is an important unit of the system. It receives multiple commands from the SCS and modulates them producing a unique Quantum Pulse that is supplied to the HSS sub-assembly for firing.

The field Rotator Sub-assembly receives rotational information from the SCS and sends it to the HSS sub-assembly for the control of field rotation. Both field rotators and signal modulators play an important role in the finally achieving the desired magnetic resonance.

QMR Guns are special cores, made of high permeability material that is precisely coiled with pure copper. There are in total 96 guns that are placed at 11.25 degrees and 3 in a sequence along the MR aperture. These guns are accurately focused at the target tissue at the time of treatment. 96 independent switching devices drive these guns from the HSS sub-assembly. Since these Guns get heated when they are firing, so a cooling system, based on heat dissipation and forced air cooling is required.

Main Control Computer is the Master control of the entire system. It is here that all treatment related computation is done. This system takes the inputs like the Cell and Tissue type, the target distance and other required parameters and computes all necessary dosage information to be passed on to the on-board SCS for starting the treatment exposures.

The following are the typical steps involved in the treatment of osteoarthritis using RFQMR:

The steps here are simple, but depends on the type of tissue that has to be regenerated. In case of Osteoarthritis; The patients are first diagnosed for Osteoarthrites by conventional x-rays. A special Computer software is used for measuring the Cartilage thickness. A High Frequency ultra sound scan of the knee is done to measure the cartilage thickness and the target distance from the surface of the skin. The RFQMR engineers will now plan the Dose parameters, from the data obtained from the scan.

Patient is loaded on the RFQMR machine and the guns are targeted precisely using a laser guided system. There are 21 exposures of one hour each every day. After the 21 days, the patients are re-evaluated.

There is a patient follow-up after 30 days after the last exposure.

CLINICAL TRIAL EXAMPLES OF TISSUE REGENERATION AND DEGENERATION

Tissue Regeneration:

The Clinical trials were involving 40 volunteers, with moderate to severe Osteoarthritis, with radiological evidence of severe disease were recruited after obtaining their informed consent. Other investigation had done included Blood tests, dynamometry etc.

The synopsis below is of one of the 40 patients have shown significant growth of cartilage tissue using RFQMR exposure. The Patient underwent 21 days of exposure for a period of one hour every day. X-rays were taken before and after exposure.

The Patient Mrs. SN, female, aged 63 years, was one of the volunteers for the RFQMR tissue regeneration study. She took the prescribed 21 RFQMR exposures. From the $7^{th}$ exposure, she was totally out of pain and was not taking any painkillers, by the $14^{th}$ exposures she could walk comfortably about 2 KM every day. The exposure continued until the $21^{st}$ day and the X-ray, Blood tests and Dynamometry was repeated.

The results were evaluated using the Knee Society rating, which is internationally accepted method to assess knee function. The result were as follows, and was better than total knee replacement.

| Assessment | Before Treatment | After Treatment |
| --- | --- | --- |
| Pain | 80% | 10% |
| Range of Motion | 44% | 60% |
| Total Knee Score | 21/100 | 73/100 |
| Total Functional Score | 30/100 | 78/100 |

The above knee society assessment score shows tissue regeneration using RFQMR can give great symptomatic relief to the patient suffering with pain due to osteoarthritis.

The patient's radiological evidence, that is more objective also showed substantial amount of tissue growth.

One can even see significant visible changes in the X-ray of the patients knee before and after the exposure. Refer FIG. 5

It is now established beyond doubt that RFQMR tissue engineering can regenerate a degenerative tissue like the cartilage, over the period of time we will be able to regenerate most human tissues using the technology.

Tissue Degeneration:

As an Index to technology proving, we had recruited 3 patients with end stage cancer, with no other medical options or surgery. These patients had estimated life expectancy ranging from 1 to 3 weeks. Here below is the case of one of them.

Patient Mr. R, with carcinoma of the lungs, operated successfully and metastatic end stage Sarcomatidcarcinoma in the abdomen, not responding to any existing therapy, the patient was in great pain and was on morphine every four hours. FIG. 6 illustrates the tumor measuring 74 mm×73 mm before RFQMR exposure. Food intake was very poor, sleep and bowl moments were erratic and irregular with severe nausea and vomiting when food intake was attempted. The patient was scheduled for 28 RFQMR exposures with assessment every 7 days considering the Disease State.

The assessment during the exposure was very encouraging and was as follows.

The severe pain totally relived by the first two exposures and gradual reduction of morphine was initiated, by the end of $4^{th}$ exposure the patient was totally out of morphine. After the third exposure, the bowls were normalised, and by the $5^{th}$ exposure the urine output increased, food intake increased nausea and vomiting stopped.

The patient developed excessive hunger, and was consuming excessive food, this soon turned to painful hunger and the patient was continuously eating. A blood test was done to assess, Blood Glucose, Liver function and blood count. This reveled that glucose was normal, Liver function was normal. The patient was put on Omeprazole, to regulate acid secretion and soon hunger was under control. An MRI (FIG. 7) scan was done after 15 exposures which indicated that the tumor has shown some non-specific changes in contrast at its core.

The exposures were continued until $28^{th}$ day. On the $30^{th}$ day a blood test was done to assess the blood count and other parameters. It was found that the patients Haemoglobin had increased from 10.1 before the start of the treatment, to 12.5 after the treatment. The patient had put on 6 kgs of weight in 28 days.

An MRI (FIG. 8) after the completion of the exposures, i.e. on the 30th Day, showed that there is clear evidence of Tissue Necrosis from the core of the Tumor covering approximately about 45% of the tumor volume. It is expected that the tissue necrosis would continue until the entire tumor is destroyed.

The patient is now symptom free, and has resumed his duties as a manager in a government Insurance Company, after 4 months.

He is being followed up every three days from the last 45 days. He is now not on any medications. The patient will report back for another MRI scan, to assess the tumor in the due course.

CONCLUSION

Considering the above two cases as example, picked out of a larger study, shows that Rotational Field Quantum Magnetic Resonance, will be a new tissue engineering method for regeneration and degeneration of human tissues that would aid in fighting many diseased states.

This new invention will go a long way in the years to come, as this is the first step to communicate with the living cell and alter their functional process. As seen above, the invention is simple to use, non-pharmaceutical and natural. This is the first time that there is a clear establishment of communication at the cellular level.

The invention claimed is:

1. A method for tissue regeneration or degeneration in human tissue comprising the steps of:
    applying field narrowed rotational focused quantum magnetic resonance to an area of treatment via a plurality of quantum resonance guns;
    rotating the field narrowed rotational focused quantum magnetic resonance around the area of treatment;
    carrying a person under treatment on a traveling platform whereby the area of treatment is moved relative to the quantum resonance guns;
    controlling the quantum resonance guns using an electronic switching system comprising a main computer having an on board microprocessor based supervisory control system for controlling, at least in part, the electronic switching system;
    using a signal modulator sub-assembly for receiving multiple commands from the supervisory control system of the main computer and for modulating the multiple commands to produce a quantum pulse that is supplied to a high speed switching assembly for firing the quantum resonance guns; and
    using a field rotator sub-assembly for receiving rotational information from the supervisory control system of the main computer and for sending the rotational information to the high speed switching assembly for the control of field rotation,
    wherein frequencies of the field narrowed rotational focused quantum magnetic resonance depend on a permittivity of a cell type and a tissue type to be treated.

2. A method to initiate or arrest cell division comprising the steps of:
    altering a cell membrane potential of a target cell in a target tissue segment by applying to the cell membrane field narrowed rotational focused quantum magnetic resonance via a plurality of quantum resonance guns, the field narrowed rotational focused quantum magnetic resonance having a modulation frequency ranging between 7 Hz to 8 MHz; and
    rotating the field narrowed rotational focused quantum magnetic resonance around the target tissue segment such that there is a frequency of switches amongst the plurality of quantum resonance guns ranging between 2 Hz to 2 KHz;
    wherein the modulation frequency and the frequency of switches amongst the plurality of quantum resonance guns depend on permittivity of the target cell and the surrounding target tissue segment, measurements of permittivity of the target cell and the surrounding target tissue segment obtainable from a standard magnetic resonance imaging machine.

3. The method as claimed in claim 2, further comprising:
    carrying a person under treatment on a traveling platform whereby the target tissue segment is moved relative to the quantum resonance guns;
    controlling the quantum resonance guns using an electronic switching system comprising a main computer having an on board microprocessor based supervisory control system for controlling, at least in part, the electronic switching system;
    using a signal modulator sub-assembly for receiving multiple commands from the supervisory control system of the main computer and for modulating the multiple commands to produce a quantum pulse that is supplied to a high speed switching assembly for firing the quantum resonance guns; and
    using a field rotator sub-assembly for receiving rotational information from the supervisory control system of the main computer and for sending the rotational information to the high speed switching assembly for the control of field rotation.

4. An apparatus for applying field narrowed rotational focused quantum magnetic resonance on a target tissue comprising:
    means for delivery of quantum magnetic resonance comprising a plurality of quantum resonance guns;
    a traveling platform for carrying a person under treatment;
    a power supply subassembly selected from the group consisting of a high current power supply sub-assembly, a high voltage power supply sub-assembly, and combinations thereof;
    an electronic switching system for controlling the quantum resonance guns comprising a main computer having an on board microprocessor based supervisory control system for controlling, at least in part, the electronic switching system;
    a power controller sub-assembly for controlling the distribution of power from the power sub-assembly;
    a high speed switching assembly;
    a signal modulator sub-assembly for receiving multiple commands from the supervisory control system of the main computer and for modulating the multiple commands to produce a quantum pulse that is supplied to the high speed switching assembly for firing the quantum resonance guns;
    a field rotator sub-assembly for receiving rotational information from the supervisory control system of the main computer and for sending the rotational information to the high speed switching assembly for the control of field rotation; and
    means for cooling and dispersing heat generated during operation of said apparatus.

5. The apparatus as claimed in claim 4, wherein the main computer calculates the field narrowed rotational focused quantum magnetic resonance to be fired based, at least in part, on a parameter selected from the group consisting of cell type, tissue type, and target distance.

6. The apparatus as claimed in claim 5, wherein the frequencies of the field narrowed rotational focused quantum magnetic resonance depend on a permittivity of the cell type and the tissue type to be treated, measurements of permittivity of the cell and the tissue type to be treated obtainable from a magnetic resonance imaging machine.

7. The apparatus as claimed in claim 4, wherein each of the quantum resonance guns is made of high permeability material that is coiled with pure copper and each of the quantum resonance guns is spaced along a magnetic resonance aperture in increments of 11.25 degrees.

* * * * *